United States Patent [19]

Jhabvala

[11] 4,308,868

[45] Jan. 5, 1982

[54] IMPLANTABLE ELECTRICAL DEVICE

[75] Inventor: Murzban D. Jhabvala, Seabrook, Md.

[73] Assignee: The United States of America as represented by the Administrator of the National Aeronautics and Space Administration, Washington, D.C.

[21] Appl. No.: 153,246

[22] Filed: May 27, 1980

[51] Int. Cl.³ .............................................. A61N 1/32
[52] U.S. Cl. .................................................. 128/421
[58] Field of Search ........... 128/419 C, 419 E, 419 F, 128/419 R, 421, 422, 784, 785, 798, 799

[56] References Cited

U.S. PATENT DOCUMENTS

| 3,654,933 | 4/1972 | Hagfors | 128/784 |
| 3,774,618 | 11/1973 | Avery | 128/784 |
| 3,881,495 | 5/1975 | Pannozzo et al. | 128/422 |
| 3,893,462 | 7/1975 | Manning | 128/419 F |
| 4,105,017 | 8/1978 | Ryaby et al. | 128/419 F |

Primary Examiner—William E. Kamm
Attorney, Agent, or Firm—John O. Tresansky; John R. Manning; Ronald F. Sandler

[57] ABSTRACT

A fully implantable and self-contained device is disclosed composed of a flexible electrode array 10 for surrounding damaged nerves and a signal generator 12 for driving the electrode array with periodic electrical impulses of nanoampere magnitude to induce regeneration of the damaged nerves.

8 Claims, 6 Drawing Figures

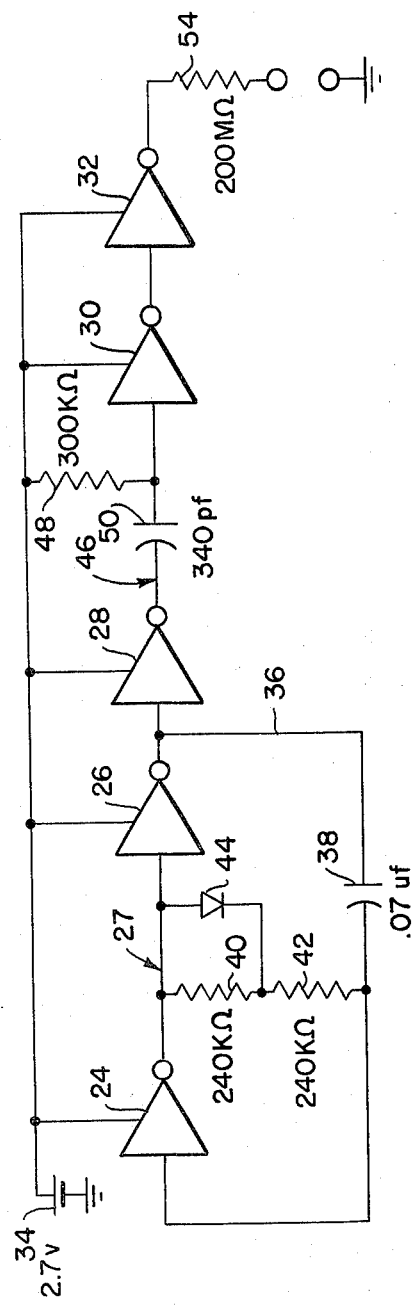
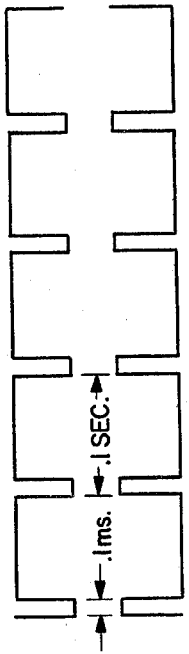
FIG. 3.
FIG. 4A.
FIG. 4B.
FIG. 4C.

IMPLANTABLE ELECTRICAL DEVICE

ORIGIN OF THE INVENTION

The invention described herein was made by an employee of the United States Government and may be manufactured and used by or for the Government for governmental purposes without the payment of any royalties thereon or therefor.

DESCRIPTION

1. TECHNICAL FIELD

This invention relates generally to implantable therapeutic devices and more particularly to an implantable device for inducing regeneration of severed nerves.

2. BACKGROUND

Medical science has progressed to the stage where devices implantable within the body have been devised for curing some of the ills of the body. Many such therapeutic devices utilize electrical energy either to render the device operational or to act on the body to affect the cure, or both. Although, in general, these prior art devices have operated satisfactorily in many medical applications, they have been found to be less than satisfactory in applications where space availability for implantables is limited or the use of a minutely sized implantable is required. Additionally, many of the existing implantable devices have energy needs which necessitate periodic re-energizing from an external energy source either through a percutaneous connector or by surgical removal of the device from the body. These energizing requirements are particularly undesirable in therapy necessitating prolonged implantation of the devices. In the developing area of regeneration of severed, or damaged, nerves by the use of implantable electrically activated devices to stimulate desired regrowth, the requirements of small size and low energy dissipation are especially acute. In addition, to avoid destruction of the nerves by overheating, the electrical energy applied by such devices must be under 200 nanoamperes in a pulsed mode.

STATEMENT OF INVENTION

Accordingly, one object of the invention is to provide a new and improved fully implantable electrically energized therapeutic device of small size and energy dissipation.

Another object of this invention is to provide an electrically energized therapeutic device capable of long term implantation.

A further object of the present invention is to provide a fully implantable therapeutic device which is self energized and capable of generating electrical impulses suitable for stimulating severed nerve regeneration.

A still further object of this invention is to provide a compact, low power dissipating and self energized source of electrical impulses of about 10 nanoamperes.

These and other objects are attained by a fully implantable self energized and small-sized electrical device formed of an array of electrodes for surrounding a damaged nerve and a signal generator for applying periodic low current impulses to the electrodes in a manner to generate electrical fields which induce regeneration of damaged nerves.

BRIEF DESCRIPTION OF DRAWINGS

In the drawings the references designate like parts throughout the several views, and wherein:

FIG. 3 is a schematic view of the signal generator of the device; and

FIG. 4 shows the waveforms at various points of the signal generator of FIG. 3.

DETAILED DESCRIPTION OF THE INVENTION

Figure 1:
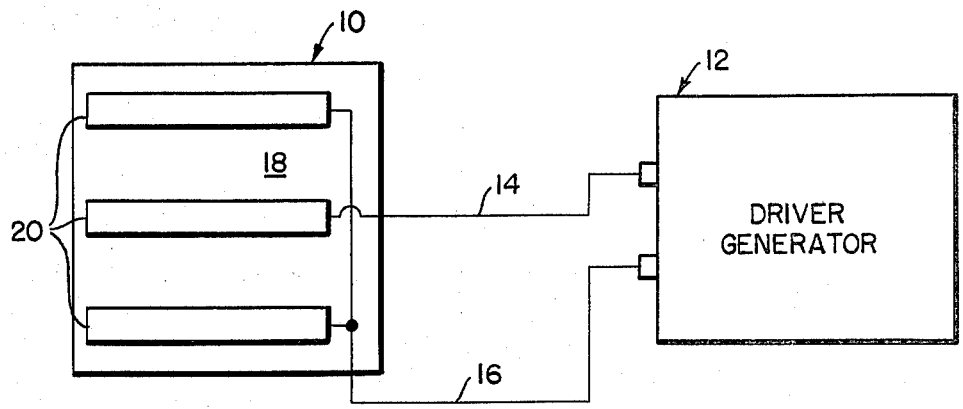
FIG. 1 is a diagrammatic view of the overall implantable device.

The implantable device of this invention is shown in FIG. 1 as being composed of an electrode array 10 and a signal generator 12 interconnected by wires 14 and 16. The signal generator provides the driving energy for the electrode array.

The electrode array is formed of a sheet 18 of flexible mesh material which is compatible with living tissue, such as Silastic. Three equal lengths of flexible wire 20 are woven within the mesh material in a parallel spaced relationship to act as electrodes. The wires are preferably made of bio-compatible platinum. The outer ones of electrodes 20 are conjointly connected by wire 16 to one output terminal of generator 12 while the center electrode is connected by wire 14 to the other output terminal.

Figure 2:
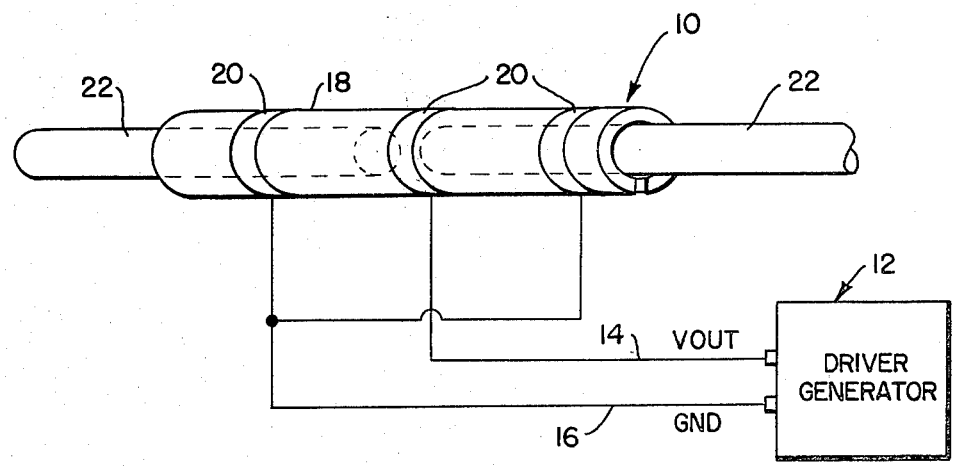
FIG. 2 is a view, partially in perspective, of the application of the device.

FIG. 2 illustrates the application of the invention to the therapeutic purpose of inducing regeneration of severed nerves of an animal. Severed nerves do not always rejoin, and when they do, they rejoin somewhat haphazardly and not directly at their endings. Because of the ionic action of nerves, it is believed that proper regeneration of severed nerves can be stimulated under the influence of electric fields which will serve to orient the severed nerves to regenerate. Such electric fields can be generated by closely wrapping electrode array 10 around an organ containing the damaged nerves 22, such for example as those present in the spinal chord of an animal, in a manner that the electrodes 20 will be substantially perpendicular to the direction of desired regeneration. In the cited example the peripheral dimensions of the array 10 may be about 1 inch square. To equally stimulate both endings of the severed nerve, the center electrode is preferably positioned at the break and each of the end electrodes are located about opposite ends of the severed nerve. It will be apparent that upon the application of an electrical signal from signal generator 12 to the electrode array 10, as connected, a potential difference of the proper polarity will be developed between the center electrode and each of the outer electrodes which will develop electric fields for orienting regrowth of the severed nerve endings toward one another.

Medical research indicates that nerve tissue will burn and can be destroyed by being subjected to the influence of certain levels of electrical energy. Thus, it is considered essential that the electrical signal applied to the electrode array be discontinuous and of a low amperage level. Signal generator 12 provides such a signal to electrode array 10.

As shown in FIG. 3, signal generator 12 consists of a plurality of inverters 24, 26, 28, 30 and 32 which are energized by a common direct current source 34. CMOS technology is employed in the inverters to reduce the energy needs of the circuit and, therefore, direct current source 34 may be a pair of watch-type disc shaped batteries of 1.35 volts each. Inverters 24 and 26 are interconnected to operate as a conventional astable multivibrator 27. Oscillation is initiated by a seed voltage, or noise, and is sustained by a feedback loop 36. A phase shifting capacitor 38 is included in the loop, which in conjunction with a pair of serially connected resistors 40, 42 sets the frequency of operation of the multivibrator stage. A diode 44 is shunted across resistor 40 to regulate the duty cycle of oscillation. With the indicated magnitude of parameters, a square wave output signal is provided by the multivibrator, as shown in FIG. 4A, with an amplitude of about 2.7 volts at a frequency of 10 Hz and a fifty percent duty cycle.

The square wave output of the multivibrator stage is applied to a conventional pulse shaping stage 46 composed of inverters 28 and 30. This stage reshapes the multivibrator output by stretching each square wave. A resistor 48 and a capacitor 50 are included to operate as a timing circuit for determining the duration of the gap between each stretched square wave, as shown in FIG. 4B. With the magnitude of parameters indicated, the output signal consists of 10 Hz pulses of about 2.7 volts amplitude with an intervening gap of 0.1 millisecond.

The output signal of the pulse shaper 46 is fed to an inverter stage 32 wherein the polarity of the output signal is inverted to provide a 0.1 millisecond pulse of about 2.7 volts at a frequency of 10 Hz. Because nerves exhibit practically zero electrical resistance, it is essential that the developed short duration pulse not be directly applied to electrode array 10 but be applied serially through a large current limiting resistor 54. With the magnitude of resistor 54 as shown in FIG. 3, the maximum level of the electrical energy to which a nerve will be subjected is an impulse of about 10 nanoamperes at a potential of about 2 volts. This amperage is well below the level of 200 nanoamperes of continuous current which is believed to be the maximum safe amount of electrical energy to which a nerve may be exposed.

A pulse generator circuit according to FIG. 3 was built on a hybrid ceramic 0.4" square and along with the batteries were encapsulated and hermetically sealed in a package about the size of a quarter coin. This generator can be operationally coupled to electrode array 10 by wires 14 and 16. Thus, it should be readily apparent that a simple, compact and low power dissipation device suitable for long duration tool implantation has been disclosed.

Accordingly, the invention having been disclosed in its best embodiment and mode of operation, that which is desired to be claimed by Letters Patent is:

1. An implantable therapeutic device comprising:
   a flexible electrode array for surrounding a nerve in its damaged area;
   circuit means for developing a continuous series of square wave pulses of electrical energy at a predetermined frequency;
   circuit means for stretching each of said square wave pulses.
   circuit means for reversing the polarity of said stretched square wave pulses to provide short duration impulses of electrical energy;
   means for energizing all of said circuit means; and
   impedance means for applying a series of said short duration impulses of electrical energy in the nanosecond range to said array to regenerate the damaged area of said nerve.

2. The device according to claim 1 wherein said electrode array includes:
   a piece of mesh material, and
   a plurality of parallel spaced electrodes woven into said mesh material.

3. The device according to claim 2 wherein the center one of said electrodes is positioned directly at the area of damage of the nerve and the remaining ones of said electrodes are positioned on opposite sides of said center one about the nerve.

4. The device according to claim 3 wherein said impedance means applies said impulses to said center one of said electrodes thereby establishing a potential difference between it and said remaining ones of said electrodes.

5. The device according to claim 4 wherein said applied impulses are less than 200 nanoamperes and of about 0.1 millisecond duration.

6. The device of claim 2 wherein the electrodes of said array are transversely disposed around said nerve with an intermediate one of said parallel spaced electrodes positioned directly at said damaged area and adjacent ones of said electrodes are positioned on opposite sides of said intermediate one.

7. The device of claims 1 or 6 wherein said impedance means discontinuously applies electrical energy to said array.

8. The device according to claim 1 wherein said impulses provided by said impedance means are about 10 nanoamperes.

* * * * *

UNITED STATES PATENT AND TRADEMARK OFFICE
Certificate

Patent No. 4,308,868                                          Patented January 5, 1982

MURZBAN D. JHABVALA

Application having been made by Murzban D. Jhabvala, the inventor named in the patent above identified, and The United States of America as represented by the Administrator of the National Aeronatics and Space Administration, the assignee, for the issuance of a certificate under the provisions of Title 35, Section 256, of the United States Code, adding the name of Donald D. Rigamonti as a joint inventor, and a showing and proof of facts satisfying the requirements of the said section having been submitted, it is this 12th day of July 1983, certified that the name of the said Donald D. Rigamonti is hereby added to the said patent as a joint inventor with the said Murzban D. Jhabvala.

Fred W. Sherling,
*Associate Solicitor*